(12) United States Patent
Van Bommel et al.

(10) Patent No.: US 8,285,399 B2
(45) Date of Patent: Oct. 9, 2012

(54) PRESENT INVENTION IS DIRECTED TO A FEEDING TUBE IN PARTICULAR FOR TOTAL PARENTAL NUTRITION AND/OR MEDICINE DOSING

(75) Inventors: Marcus Jozef Van Bommel, Waalre (NL); Aaldert Elevelt, Best (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 344 days.

(21) Appl. No.: 12/513,216

(22) PCT Filed: Nov. 9, 2007

(86) PCT No.: PCT/IB2007/054556
§ 371 (c)(1),
(2), (4) Date: May 1, 2009

(87) PCT Pub. No.: WO2008/059415
PCT Pub. Date: May 22, 2008

(65) Prior Publication Data
US 2010/0087715 A1    Apr. 8, 2010

(30) Foreign Application Priority Data
Nov. 16, 2006    (EP) .................................... 06124180

(51) Int. Cl.
*A61N 1/00* (2006.01)
*A61B 5/00* (2006.01)
*A61B 5/04* (2006.01)
*A61B 5/05* (2006.01)

(52) U.S. Cl. ......... 607/124; 600/301; 600/380; 600/424

(58) Field of Classification Search .................. 600/380, 600/393, 509, 547, 593; 607/124
See application file for complete search history.

(56) References Cited

U.S. PATENT DOCUMENTS

| 4,381,011 A | 4/1983 | Somers, III |
| 4,836,214 A | 6/1989 | Sramek |
| 5,179,952 A | 1/1993 | Buinevicius et al. |
| 5,983,126 A | 11/1999 | Wittkampf |
| 2004/0102710 A1 | 5/2004 | Kim |
| 2010/0179417 A1* | 7/2010 | Russo ........................... 600/424 |

FOREIGN PATENT DOCUMENTS

DE    19823146 C1    7/1999
(Continued)

OTHER PUBLICATIONS

Brengelmann, G. L. et al.; Electrocardiographic verification of esophageal temperature probe position; 1979; J. of Applied Physiology; 47(3)abstract.

*Primary Examiner* — Linda Dvorak
*Assistant Examiner* — Brian M Antiskay

(57) ABSTRACT

The present application is directed to a feeding tube in particular for total parental nutrition and/or medicine dosing. The feeding tube functionality is combined with internal monitoring of vital functions, such as ECG, PH, etc. The position of the electrodes is essential for measuring the optimal signal. In the present application the optimal position is determined by measuring the inversion point of the ECG signal. During insertion of the catheter or modified feeding tube the ECG signal is continuously monitored. Via an acoustic signal the strength of the signal is notable. This enables the nursing staff a simple control of the insertion process.

15 Claims, 2 Drawing Sheets

FOREIGN PATENT DOCUMENTS

| WO | 8500982 | A1 | 3/1985 |
| WO | 03077759 | A1 | 9/2003 |
| WO | 2005115234 | A1 | 12/2005 |
| WO | 2005117690 | A1 | 12/2005 |
| WO | 2006015230 | A2 | 2/2006 |
| WO | 2006060458 | A1 | 6/2006 |

\* cited by examiner

PRESENT INVENTION IS DIRECTED TO A FEEDING TUBE IN PARTICULAR FOR TOTAL PARENTAL NUTRITION AND/OR MEDICINE DOSING

In hospitals many vital functions, such as ECG, SpO2, respiratory motion, etc, are measured to monitor patients. Traditionally, this is done using detectors, such as electrodes on the outside of the patient. Oesophageal physiological monitoring offers an advantage in terms of the reliability and accuracy of signals. For Intensive care patients and immature babies a feeding tube is often needed to feed and to provide medicine. In case of premature neonates even more than 90% of these neonates in Intensive care are very immature and are therefore fed by feeding tubes. Sensors for detecting and recording the above functions can be combined with the oesophageal feeding tube or a catheter.

For intensive care patient and also for neonatal children there is a need for continuously monitoring the ECG signal for sometimes several weeks. Currently sensors are attached the skin on the chest to record those signals. During handling of the sensors, the skin can be damaged and makes it more susceptible for infections.

Special care must be exercised in handling and monitoring of premature birth infants, which are often very thin and fragile and light weighted. The skin is very sensitive and easily bruised such that superficial damage may occur when a monitor lead is placed on the infant's body for a even short period of time. In addition, skin injury may be caused by tape or electrode adhesives. Survival of many premature birth infants requires minimal manipulation or interference to thus prevent unnecessary stress or injury.

Internal monitoring of vital functions offers the advantage not to bruise the patient's skin. The oesophagus is an ideal place to monitor several functions of a patient as it is close to heart and lungs and has a good conduction for electrical signals. Compared to present used monitoring techniques, in which electrodes are attached to the skin, no skin damage will occur, nor do external electrical wires hamper medical therapy and nursing care, if a modified oesophageal feeding tube is used.

A modified feeding tube enables to get a higher accuracy of the signals and to have the ability of measuring parameters, which cannot be determined from the outside. Furthermore, there is no need to have all the wires and sensors on the outside of the patient, which can improve the handling speed of hospital personnel.

However, the position of the internal sensors within the feeding tube is highly determining the accuracy of the signals. The sensor has to be placed at a fixed distance above the lower oesophageal sphincter (LES). The relationship between distance from nares to LES and postmenstrual age (PMA), body lengths, body weight, and head circumference have been used to determine the optimal lengths and positioning of the feeding tube.

Recent studies have indicated that the relationship between the distance from nares to LES are dependent on age and size in a population of premature infants. Existing formula for the estimation of LES position allow a good estimation of the length and the positioning of the feeding tube for grown up patients but instead are inaccurate in premature infants. The use of these formulas for the purposes of positioning will result in the sensor being position to close to the LES with the possibility that clinically misleading data will be obtained or the electrodes of the sensor are not located at the optimal position resulting in a non-optimal signal of the sensor.

In this coherence U.S. patent number WO 2005/115234 focuses mainly on a method of easy positioning the feeding tube together with the electrodes in the oesophagus of the neonate patients. The patent claims the relation between the optimal position of the proximal electrode and the circumference of a neonatal child. However, this is not unambiguous e.g. for children with an abnormality of the circumference of the head so that the method cannot be used in these cases.

It is therefore an object of the present application to provide a feeding tube which more effectively makes use of a combined monitoring and feeding functionality by creating a simple and effective way of positioning the feeding tube in a patient's oesophagus.

The feeding tube according to the present application may be used as part of a trigger system that electrically detects the optimal position of electrodes in the esophagus. Therefore the feeding tube according to the present application includes at least one sensing means for internal monitoring a patient's vital functions, one of the sensing means being an ECG signal monitoring device continuously monitoring a patient's ECG signal wherein the ECG signal is used as an assisting means for placing the feeding tube in a patient's esophagus in an optimal position. During the insertion of the feeding tube the strength of the signal changes in a typical way. This change in strength can be displayed on a monitor and also be made acoustic. This allows the nursing staff to draw conclusions from these changes and thus to simply control the insertion process. This results in a very easy way of handling and a more accurate placement of the feeding tube in the esophagus.

One preferred way to carry out the present application is to measure the ECG signal as a function of the position of the feeding tube, wherein an inversion of the ECG signal indicates a position, which may be deemed to be the optimal position of the feeding tube in the esophagus or which may act as a reference position from which the feeding tube may be moved a pre specified distance within the patient's esophagus to reach an optimal position.

According to one aspect of the present application the ECG signal monitoring device comprises two ECG sensor electrodes, one being placed facing a distal end of the feeding tube and at least one electrode facing a proximal end of the feeding tube wherein the two electrodes may be spaced from each other with a distance of 0.5 cm to 5 cm, preferably 1 cm to 4 cm, more preferably 1 cm to 2 cm to get reliable measurement results.

The distance between the distal end of the feeding tube and the electrode facing the distal end of the feeding tube may be chosen depending on the size of the patient to be monitored. There may be certain standard sizes for example five different sizes matching five different ranges of development stages of the premature children depending for example on size and weight of the patient as well as one or two standard sizes for grown up patients with a differentiation in for example male or female patients.

In one preferred embodiment of the present application the ECG signal detected by the sensing means may after insertion into the patient's esophagus also indicate a displacement of the feeding tube. Therefore the inversion point of the ECG signal may serve as a reference position and in this case may be deemed to be the optimal position of the feeding tube in the esophagus. Since a displacement in direction to the stomach is not as harmful as in the opposite direction, the feeding tube should be inserted into the esophagus until the insertion point has been reached or to move a little further. If after a while the feeding tube moves in the opposite direction and crosses the inversion point of the ECG signal again a sound may be generated by a warning means to indicate the displacement to the medical staff.

A non-invasive patient assessment and monitoring system in particular for total parental nutrition and/or medicine dosing may comprise a feeding tube according to the present application, furthermore: an electronic system adapted to receive data from the at least one sensing means of the feeding tube the electronic system including as a positioning assisting means a monitor and/or an acoustic signal generator, wherein while placing the feeding tube into a patient's esophagus a sound may be generated by the electronic system depending on the position of the feeding tube within the esophagus to assist the medical staff. Without this assisting sound the medical staff would have to monitor the display showing the ECG signal to know when the inversion point of the ECG signal has been reached thereby making it impossible to concentrate solely on the patient and on the handling of the feeding tube. By creating a sound it is not necessary to monitor the display the whole time, which makes the handling easier and the medical staff is able to choose a most convenient position to accomplish the treatment of the patient. The sound may for example be generated if the ECG signal monitoring device reaches an inversion point of the ECG-signal. It is also possible to constantly generate an acoustic signal and to generate an additional signal or to generate a change in signal at the position at which the ECG signal is inverted an indicating that the optimal position is reached. The thus described method enables the use of recording of ECG and other signals via internal electrodes for the mentioned class of patients as a routine clinical practice. This will result in a reduction of the handling time per patient and a more accurate placement of the feeding tube even if the person is not very experienced.

The system according to the present application in one embodiment includes a feeding tube comprising more than two electrodes to allow an all-round monitoring of the vital parameters or other important parameters being self-evident in particular in intensive care treatment. The feeding tube may for example include a plurality of sensors interconnected to said feeding tube, said sensors including at least a thermistor, a plurality of electrodes in particular for an impedance measurement, a pH sensor and an ultrasound sensor wherein the feeding tube is interconnected to the electronic system adapted to receive data from said sensors relating to at least one of a body temperature, blood flow, heart rate, respiration, and PH-value, and assign a score reflective of the patient's vital condition. It is understood, that these functions have only an exemplary character and the use of the system is not restricted to these applications.

The non-invasive patient assessment and monitoring system according to the present application may further comprise an algorithm adapted to monitor and/or indicate the onset of changes in the patient's condition and/or predict changes in the patient's condition. A storage means may save a patient's data so that a course of disease or recovery can be retrieved at a later stage by a physician or the medical staff to decide how to proceed with the medical treatment.

A non-invasive patient assessment and monitoring system and a modified feeding tube, which meet the abovementioned objects and provide other beneficial features in accordance with the presently preferred exemplary embodiment of the present application will be described below with reference to FIGS. 1 and 2.

Those familiar with the state-of-the-art will readily appreciate that the description given herein with respect to those figures is for explanatory purposes only and is not intended to limit the scope of the invention.

Figure 1:
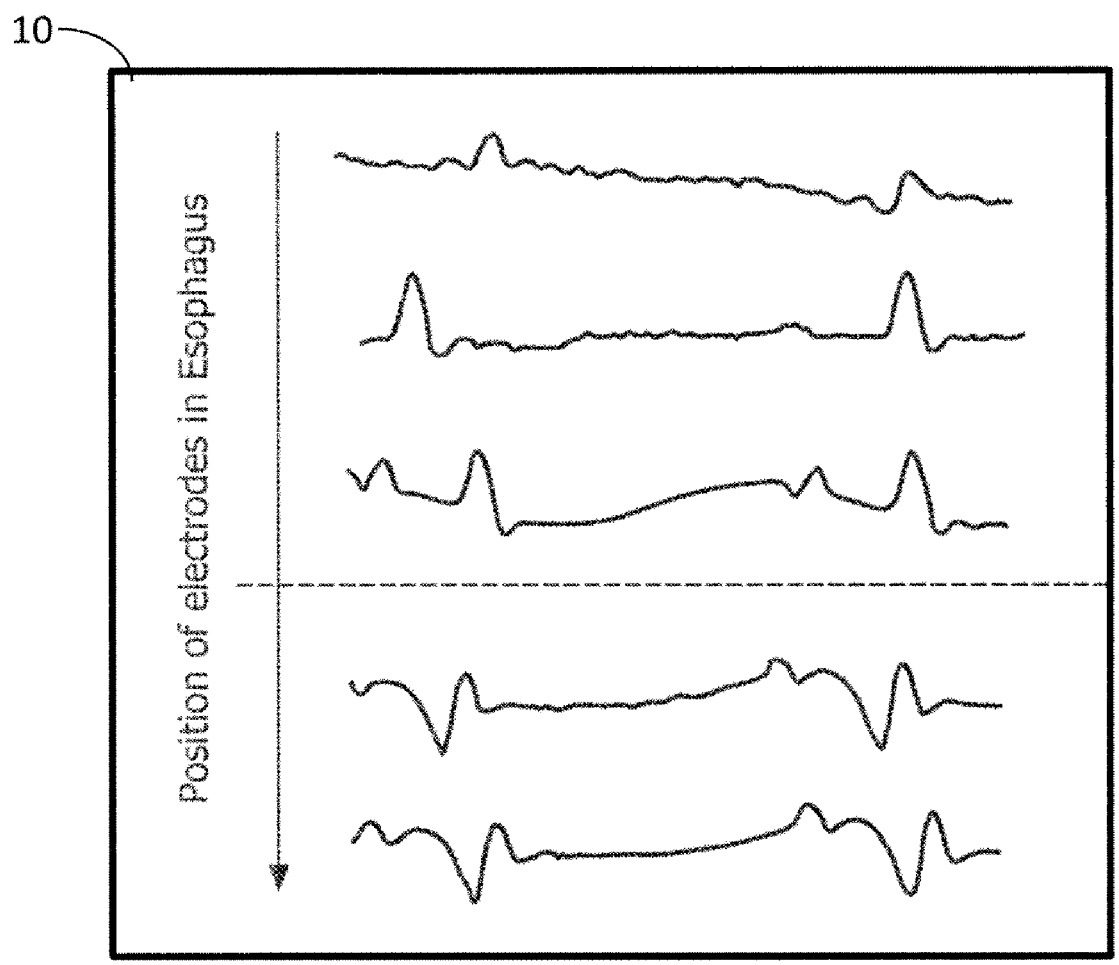
FIG. 1 shows an ECG signal measured via an ECG signal monitoring device as a function of the position of the feeding tube in the esophagus.

In FIG. 1 an ECG signal is given as a function of the position of the feeding tube 1 in the oesophagus. The feeding tube 1 comprises at least two electrodes 2 for sensing the ECG signal. During the insertion of the feeding tube 1 the strengths of the signal changes in a typical way. At a too high distance of the electrodes 2, the signal is to weak. When the distance is lowered the signal increases until one of the electrodes 2, e.g. the electrode 2 at a distal end 3 of the feeding tube 1 comes below the heart position. At that point the ECG signal is inverted. The moment and the position where the signal is inverted can be detected and is an indication for the position of the electrodes 2 within the oesophagus. Therefore, the ECG signal is used as an assisting means for placing the feeding tube 1 in the patient's oesophagus in an optimal position. This allows a nursing staff to draw conclusions from these changes and thus to simply control the insertion process. This results in a reduction of handling per time per patient and a more accurate placement of the feeding tube 1. The diagram of the ECG signal is to be red top down.

In one embodiment of the present application the inversion point of the ECG signal may indicate a position, which may be deemed to be the optimal position of the feeding tube 1 in the oesophagus. Alternatively, the inversion point may act as a reference position for which the feeding tube 1 has to be moved a pre-specified distance within the patient's oesophagus to reach the optimal position.

After the feeding tube 1 has been inserted in the patient's oesophagus the ECG signal detected by the sensing means 2 is used as an indicator of a displacement of the feeding tube 1. Therefore, also the inversion point of the ECG signal serves as a reference position and in this case is deemed to be the optimal position of the feeding tube 1 in the oesophagus or may be deemed to be the limitation of the maximum displacement of the feeding tube 1 in the oesophagus. Since a displacement in direction to the stomach is not as harmful as in the opposite direction, the feeding tube 1 should be inserted into the oesophagus until the inversion point has been reached or should be moved a little further. If the feeding tube 1 afterwards moves back in the opposite direction and crosses the inversion point of the ECG signal again, a sound is generated by a warning means to indicate that the displacement has exceeded a pre-determined threshold.

Figure 2:
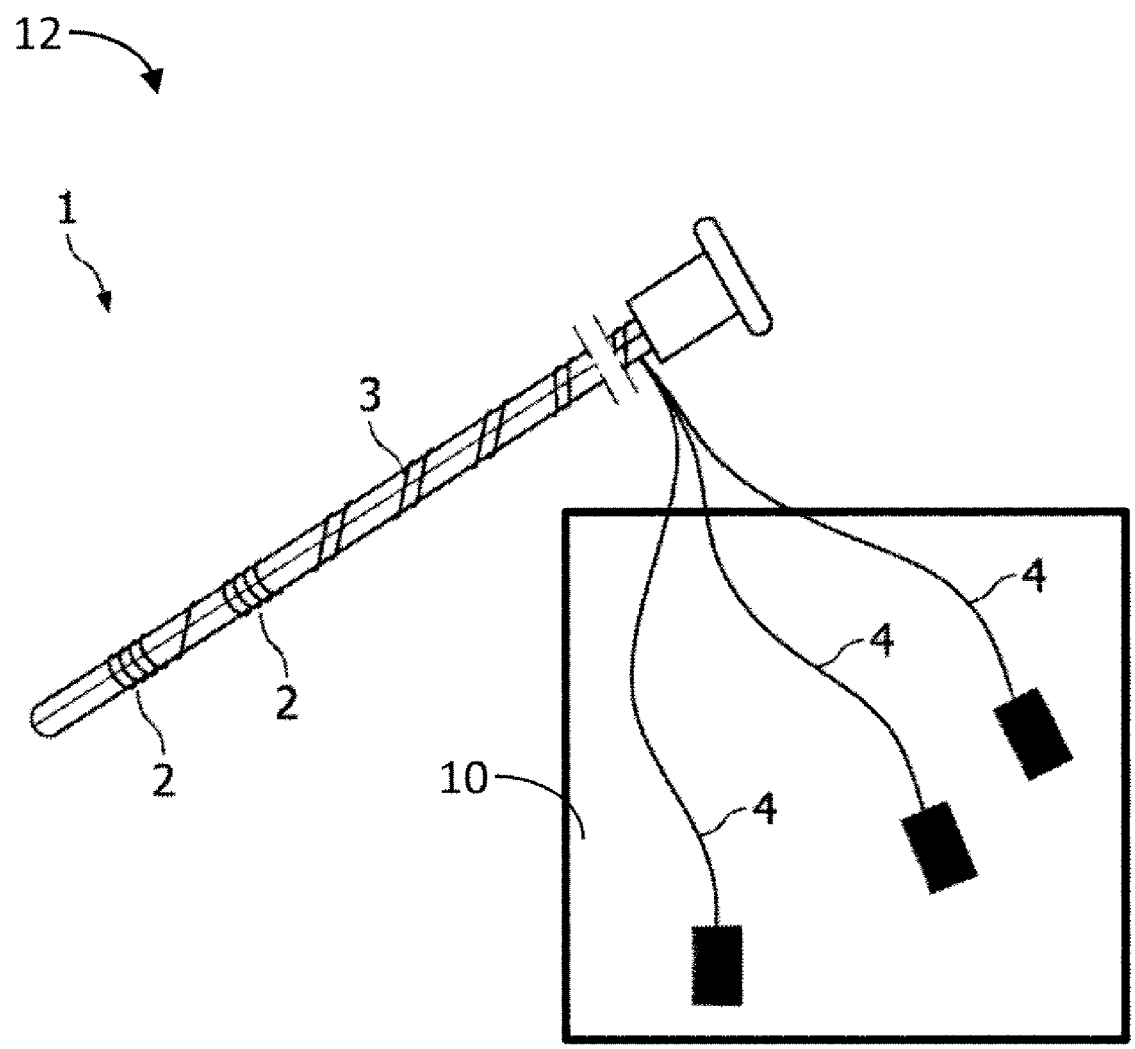
FIG. 2 shows a perspective view of the modified feeding tube according to the present application.

FIG. 2 shows a perspective view of a modified feeding tube 1 according to the present application. At the outside of the modified feeding tube 1 one electrode 2 is arranged at the distal end 3 of the feeding tube 1 and one electrode 2 is provided at the proximal end of the feeding tube 1. These two electrodes 2 together build an ECG signal monitoring device 10 which is able to continuously monitor a patient's ECG signal even over a period of several weeks. The two electrodes 2 are spaced apart from each other with a distance of one to four centimetres. The distance between the distal end 3 of the feeding tube 1 and the electrodes 2 facing the distal end 3 of the feeding tube 1 is chosen depending on the size of a patient to be monitored.

FIG. 2 shows a perspective view of the modified feeding tube 1 according to the present application. The feeding tube 1 is part of a non-invasive patient assessment and monitoring system 12 and includes a plurality of sensors 2 interconnected to the feeding tube 1. In this embodiment the sensors 2 include a thermistor, and a plurality of electrodes in particular for a four point impedance measurement, a pH sensor and an ultrasound sensor (not shown in detail) for conducting measurements regarding the body temperature, the blood flow, the heart rate, respiration, acidity and to assign a score reflective of the patient's vital condition. The electronic system is adapted to receive data via a wiring 4 from said sensors 2 and comprises an algorithm adapted to monitor and to indicate the onset of changes and to predict changes in the patient's condition. It is understood that these named functions have only an exemplary character and the use of the system is not restricted to these applications.

While placing the feeding tube 1 into a patient's oesophagus in addition to the visible signal according to FIG. 1 a sound may be generated by the electronic system depending on the position of the feeding tube 1 within the oesophagus to assist the medical staff. Without the assisting sound the medical staff would have to continuously monitor the display showing the ECG signal to know when the inversion point of the ECG signal has been reached. This makes it impossible to concentrate solely on the patient and makes the handling of the feeding tube 1 more difficult, so that only very experienced personnel is able to conduct the placing. By creating an acoustic signal it is not necessary to monitor a display reproducing the ECG signal the whole time, which makes the handling easier and medical staff is able to choose a most convenient position to accomplish the treatment of the patient. The acoustic signal either may be generated if the ECG signal monitoring device 10 reaches the inversion point of the ECG signal or may be continuously generated and may change if the inversion point has been reached or even exceeded. This will result in a reduction of the handling time per patient and in a more accurate placement of the feeding tube 1 even if the personal is not very experienced.

The invention has been described with reference to the preferred embodiments. Modifications and alterations will occur to others upon a reading and understanding of the preceding detailed description. It is intended that the invention be construed as including all such modifications and alterations insofar as they come within the scope of the appended claims or the equivalents thereof.

The invention claimed is:

1. A feeding tube for at least one of total parental nutrition and medicine dosing of a patient comprising: a tubular member configured to carry at least one of nutrients and medicine; at least one sensor interconnected to the tubular member for internal monitoring of a patient's vital functions, one of the sensors being connected with an ECG signal monitoring device which continuously monitors an ECG signal of the patient; and the ECG signal monitoring device using the ECG signal for positioning the feeding tube in an esophagus of the patient in an optimal position; wherein the ECG signal is measured as a function of the position of the feeding tube and an inversion of the ECG signal indicates a position, which acts as a reference position from which the feeding tube is moved a pre-specified distance within the patient's esophagus to reach the optimal position; and wherein the ECG signal monitoring device generates an acoustic signal in response to the feeding tube position crossing an inversion point of the ECG signal.

2. The feeding tube according to claim 1, wherein the ECG signal monitoring device includes at least two electrodes being placed near a distal end of the feeding tube.

3. The feeding tube according to claim 2, wherein the two electrodes are spaced from each other with a distance of 1 cm to 4 cm.

4. The feeding tube according to claim 3, wherein the distance between a distal end of the feeding tube and an electrode facing the distal end of the feeding tube depends on the size of the patient to be monitored.

5. The feeding tube according to claim 1, wherein variations of the ECG signal detected by the at least one sensor indicates a displacement of the feeding tube within the patient's esophagus.

6. The feeding tube according to claim 5, wherein the ECG signal monitoring device generates a signal upon detection of a displacement of the feeding tube within the esophagus.

7. A non-invasive patient assessment and monitoring system for total parental nutrition and/or medicine dosing comprising: a feeding tube including a plurality of sensors for internally and continuously monitoring an ECG signal of a patient; an electronic monitoring system which receives data from the sensors and includes a positioning assisting monitor and an acoustic signal generator, wherein while placing the feeding tube into an esophagus of the patient, the ECG signal is displayed at the monitor and a sound is generated by said acoustic signal generator in response to the at least one electrode reaching a point in the esophagus in which the ECG-signal inverts.

8. The non-invasive patient assessment and monitoring system according to claim 7, wherein the sensors including at least one of a thermistor, a plurality of electrodes for an impedance measurement, a pH sensor and an ultrasound sensor and the electronic system is adapted to receive data from said sensors relating to at least one of a body temperature, blood flow, heart rate, respiration, and PH sensor and assign a score reflective of the patient's vital condition.

9. The non-invasive patient assessment and monitoring system according to claim 7, wherein the electronic system further includes a processor which implements an algorithm which at least one of monitors and indicates the onset of changes in the patient's condition or predicts changes in the patient's condition.

10. The feeding tube according to claim 1, wherein the signal generated by the ECG signal monitoring device is an audio signal.

11. The feeding tube according to claim 10, wherein the ECG signal monitoring device generates a constant audio signal upon detection of a displacement of the feeding tube within the esophagus and at least one of changes the constant audio signal and generates an additional audio signal in response to the feeding tube position crossing the inversion point of the ECG signal.

12. The non-invasive patient assessment and monitoring system according to claim 7, wherein the signal generated is an audio signal.

13. The non-invasive patient assessment and monitoring system according to claim 12, wherein the electronic system generates a constant audio signal during detection of displacement of the feeding tube within the esophagus and at least one of changes the constant audio signal or generates an additional audio signal in response to the feeding tube position crossing a point at which the ECG signal inverts.

14. A method comprising:

inserting a feeding tube into an esophagus;

during insertion, monitoring a patient's ECG signal using at least one sensor interconnected to the feeding tube;

determining a position of the feeding tube utilizing the monitored ECG signal, the ECG signal being measured as a function of a position of the feeding tube in the esophagus; and generating an audio signal in response to upon detection of the feeding tube approaching an optimal position.

15. The method according to claim 14, further including:

generating a constant audio signal upon detection of a displacement of the feeding tube within the esophagus; and changing the constant audio signal in response to the feeding tube position crossing the inversion point of the ECG signal.

\* \* \* \* \*